United States Patent
Katsumoto

(10) Patent No.: US 8,211,029 B2
(45) Date of Patent: Jul. 3, 2012

(54) DEVICES, SYSTEMS, AND METHODS FOR ACCURATE BLOOD PRESSURE MEASUREMENT

(75) Inventor: Kenichi Katsumoto, Tokyo (JP)

(73) Assignee: Memsic, Inc., Andover, MA (US)

( * ) Notice: Subject to any disclaimer, the term of this patent is extended or adjusted under 35 U.S.C. 154(b) by 374 days.

(21) Appl. No.: 12/548,690

(22) Filed: Aug. 27, 2009

(65) Prior Publication Data
US 2011/0054329 A1 Mar. 3, 2011

(51) Int. Cl.
*A61B 5/02* (2006.01)
(52) U.S. Cl. .......... 600/490; 600/503; 600/595
(58) Field of Classification Search .......... 600/485, 600/490–497, 500–504, 300, 595; 73/1.75, 73/1.77, 1.78; 463/36–37, 39
See application file for complete search history.

(56) References Cited

U.S. PATENT DOCUMENTS

| | | | |
|---|---|---|---|
| 5,778,879 A | 7/1998 | Ota et al. | |
| 6,782,182 B2* | 8/2004 | Dautartas et al. | 385/137 |
| 7,101,338 B2* | 9/2006 | Yang | 600/485 |
| 7,316,653 B2 | 1/2008 | Sano et al. | |
| 7,326,180 B2 | 2/2008 | Tanabe et al. | |
| 7,364,548 B2 | 4/2008 | Shirasaki et al. | |
| 7,367,952 B2 | 5/2008 | Sawanoi et al. | |
| 7,409,863 B2* | 8/2008 | Bateman et al. | 73/705 |
| 7,453,390 B2 | 11/2008 | Nishiguchi et al. | |
| 2004/0199081 A1* | 10/2004 | Freund et al. | 600/485 |
| 2007/0032748 A1* | 2/2007 | McNeil et al. | 600/595 |
| 2007/0276266 A1* | 11/2007 | Baba | 600/490 |
| 2010/0049059 A1* | 2/2010 | Ha et al. | 600/485 |

OTHER PUBLICATIONS

Omron Healthcare, Inc., Instruction Manual, "Wrist Blood Pressure Monitor with Advanced Positioning Sensor (APS)", Model HEM-637, 2006, 17 pgs.

* cited by examiner

*Primary Examiner* — Michael Kahelin
*Assistant Examiner* — Eric Messersmith
(74) *Attorney, Agent, or Firm* — Weingarten, Schurgin, Gagnebin & Lebovici LLP

(57) ABSTRACT

A multiple-axis accelerometer for use with a blood pressure monitor or a blood pressure measuring device (BPM) to determine an inclination associated with the point of fixture. The accelerometer is attached to a substrate that is structured and arranged in a vertical or substantially vertical plane. The accelerometer includes a first accelerometer portion that is adapted to generate a first output based on acceleration in a first direction in the vertical plane ($A_x$); and a second accelerometer portion that is adapted to generate a second output based on acceleration in a second direction, orthogonal to the first direction, in the vertical plane ($A_y$). The first and second outputs provide a measure of the inclination about an axis that is orthogonal or substantially orthogonal to the vertical plane. The measured inclination is a roll angle ($\gamma$) is given by the formula:

$$\gamma = \arctan(A_y/A_x).$$

The polarity of the roll angle determines dynamically whether the point of fixture is to the right or the left appendage or extremity.

9 Claims, 1 Drawing Sheet

DEVICES, SYSTEMS, AND METHODS FOR ACCURATE BLOOD PRESSURE MEASUREMENT

CROSS REFERENCE TO RELATED APPLICATIONS (Not applicable)

STATEMENT REGARDING FEDERALLY SPONSORED RESEARCH OR DEVELOPMENT (Not applicable)

BACKGROUND OF THE INVENTION

Devices, systems, and methods for accurately measuring blood pressure are disclosed and, more specifically, devices, systems, and methods that use inclination from a vertical or substantially vertical orientation to properly position the blood pressure monitor with respect to the subject's myocardium and to determine, inter alia, to which wrist the blood pressure monitor is attached.

Non-invasive, oscillometric blood pressure monitors (BPMs) are adapted to sense pulsewaves generated by the beating of the myocardium and the blood flow of a mammalian subject, precluding the need for more-subjective, auscultatory methods that require use of a stethoscope and/or of a human ear. Conventionally, BPMs include a pressure-applying device, e.g., a cuff, a sensing device, and a processing device. The cuff is applied to an external surface—usually an appendage, extremity or digit—of the mammalian subject. Then a controllable pressure is applied through the cuff to the external surface until the mammalian subject's local artery is occluded.

Once the local artery has been occluded, the sensing device detects and, in some instances, records pulsewave data corresponding to movement of the mammalian subject's myocardium and/or the pulsing of blood through the mammalian subject's arteries. The sensing device generates pulsewave data, which it transmits to the processing device. From pulsewave data, the processing device calculates pressure data, from which the maximum arterial pressure (systolic) and minimum arterial pressure (diastolic) are determined.

Conventionally, a blood pressure monitor (BPM) is affixed to some portion of a mammalian body part, e.g., a finger tip, wrist, upper arm, and the like, which is further positioned at or substantially at the same or substantially the same elevation as the mammalian subject's myocardium. Error results whenever the myocardium and BPM are not positioned at the same elevation. Indeed, if the BPM is located below the myocardium, measured or estimated blood pressure levels will be slightly higher than true, while if the BPM is located above the myocardium, pressure levels will be slightly lower than true.

The prior art includes electronic BPMs having a posture detector that is adapted to evaluate a relationship between the inclination of the electronic BPM with respect to a horizontal surface. These devices are designed to maintain the electronic BPM between an upper inclination limit (b) and lower inclination limit (a), which is approximately at or substantially at the same elevation as the myocardium.

This approach, however, introduces further measurement error when the subject has an abnormal size (height or relative body dimensions) that might cause the mammalian subject's myocardium not to be at the same elevation as the electronic BPM. Moreover, this approach typically only measures a pitch angle, further assuming that the forearm distance between the elbow resting on the horizontal place and the BPM located at the subject's wrist is the same for all subjects.

Conventional BPMs also suffer from a lack of "ambidexterity", which is to say that the devices include one program for when the BPM is affixed to the left wrist and a second program for when the BPM is affixed to the right wrist. Failure to use the BPM on the correct extremity or incorrectly inputting the correct extremity of application, may result in inaccurate blood pressure measurements.

Accordingly, it would be desirable to provide a BPM that takes into account a roll angle, to provide better accuracy by detecting the proper position of the BPM. It would also be desirable to provide a BPM that is "ambidextrous", which is to say that, the BPM is able to determine internally to which wrist the device is attached without requiring user input.

BRIEF SUMMARY OF THE INVENTION

In accordance with the present invention, devices, systems, and methods for more accurately measuring blood pressure of a mammalian subject are disclosed. The invention includes an improvement to a device for measuring or monitoring blood pressure in a mammal.

The improvement includes a multi-axis, i.e., a three-axis, accelerometer that is adapted to generate acceleration data for use in estimating a roll angle and change in roll angle of the sensor. Preferably, the accelerometer is disposed on a substrate that is oriented vertically or substantially vertically in a plane and is adapted to measure acceleration in at least two orthogonal directions about an axis that is orthogonal or substantially orthogonal to the vertical plane of the substrate.

More preferably, the accelerometer includes a first accelerometer portion that is adapted to generate a first output ($A_x$) based on acceleration measured in a first direction in the vertical plane; a second accelerometer portion that is adapted to generate a second output ($A_y$) based on acceleration measured in a second direction, which is orthogonal to the first direction, in said vertical plane; and means for transmitting first and second acceleration output data to the controller unit. The first and second acceleration output data transmitted to the controller unit are used to estimate a roll angle ($\gamma$) over a wide pitch angle using the formula:

$$\gamma = \arctan(A_y/A_x).$$

Advantageously, the estimated roll angle has a polarity that is indicative of whether the apparatus is affixed to a left wrist or to a right wrist of the subject. This allows the device to be "ambidextrous" without having to preset the device by designating one extremity or the other.

A method for dynamically positioning a sensor of a blood pressure measurement apparatus and/or a blood pressure monitoring apparatus proximate to a myocardium of a mammalian subject to provide more accurate blood pressure readings and a method for dynamically determining whether a sensor of a blood pressure measurement apparatus or a blood pressure monitoring apparatus is on a left wrist or a right wrist of a mammalian subject are disclosed.

Other aspects, features, and advantages of the present invention will be apparent from the Detailed Description that follows.

BRIEF DESCRIPTION OF THE SEVERAL VIEWS OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

An inclination measuring device (the "inclinometer" or "device") for use with a blood pressure monitor (BPM) is disclosed. The inclinometer includes a multiple-axis, i.e., a two-axis or three-axis, accelerometer that is adapted to measure the inclination, i.e., the pitch and roll angles, about an axis that is orthogonal or substantially orthogonal to a vertical plane. The embodied inclinometer further includes a controller unit that is adapted to use the acceleration data from the multiple-axis accelerometer to determine whether the BPM has been affixed to the subject's left or to the subject's right wrist or arm, e.g., using the polarity of the acceleration data and the roll angle. Moreover, using the acceleration data and the roll angle, the inclinometer is adapted to position the BPM more reliably and expertly at the elevation of the subject's myocardium, to generate more true blood pressure measurements.

Figure 1:
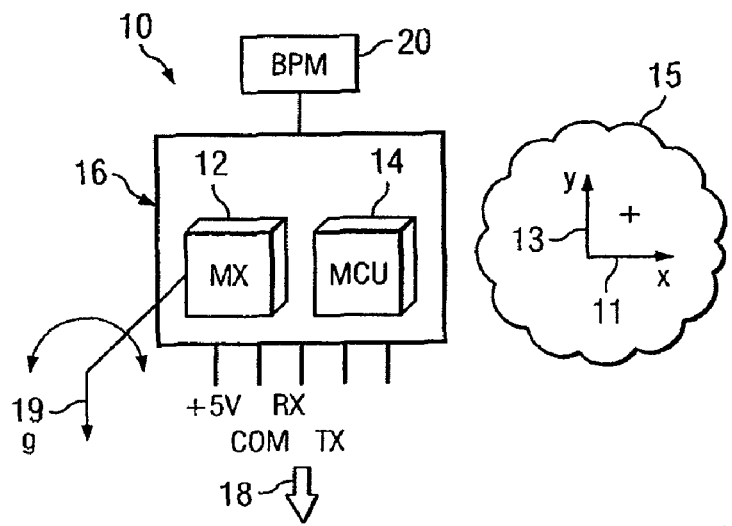
FIG. 1 shows a 360-degree inclinometer in accordance with the present invention.

FIG. 1 shows an inclination measuring device 10 for use with a BPM. The device 10, e.g., an inclinometer or, more particularly, a 360° inclinometer, includes a multiple-axis accelerometer (MX) 12 and a controller unit (MCU) 14, which are mounted on a common substrate 16, e.g., a daughter printed circuit board (PCB), or on separate substrates (not shown). For reasons that will become more evident below, the device 10 is arranged vertically and the multiple-axis accelerometer is adapted to measure acceleration 360° about an axis 19 that is orthogonal or substantially orthogonal to the vertical plane 15.

As a result, when the device 10 is stationary, which is to say that when there are no lateral (x-axis 11) or vertical (y-axis 13) accelerations acting on the device 10, the only force acting on the device 10 is that which is due to the force of gravity. Moreover, acceleration data generated by the multiple-axis accelerometer 12 can be used to determine an inclination angle (γ), i.e., the roll angle of the accelerometer 12. The polarity of inclination measurement data enables the device 10 to determine whether the device 10 or, more particularly, the BPM is located on the subject's left or the subject's right wrist or arm.

As is well known to those of ordinary skill in the art, the human myocardium is normally slightly offset to the left of center. Therefore, BPM positioning signals corresponding to the left arm or wrist will differ slightly from BPM positioning signals corresponding to the right arm or wrist. As a result, prior, active designation of indication of "left wrist" or "right wrist" is unnecessary, which saves data storage space.

Acceleration Data and Roll Angle

Figure 2:
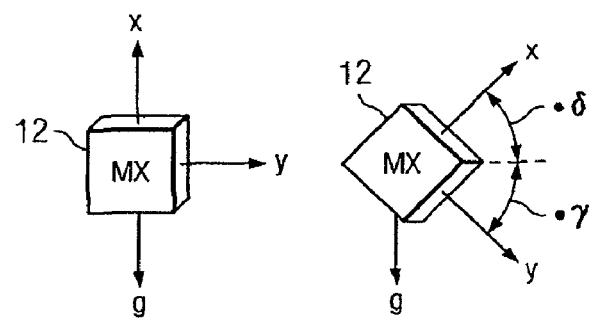
FIG. 2 shows a single axis inclination from the vertical of a multiple-axis accelerometer in accordance with the present invention.

More specifically, referring to the free-body diagram in FIG. 2, the relationship between acceleration outputs ($A_x$ and $A_y$) and inclination angles (δ and γ), which correspond to pitch and roll angles, respectively, can be expressed as follows:

$$A_x = g \cdot sin(\delta) \qquad [1]$$

and $$A_y = g \cdot sin(\gamma) \qquad [2].$$

where "g" refers to the acceleration to gravity (32.2 ft/sec$^2$) and, by design, where δ+γ=90° [3]. Substituting Eqn. [3] into Eqn. [1], $$A_x = g \cdot sin(\gamma - 90°) = g \cdot cos(\gamma) \qquad [4].$$

The ratio of Eqn. [2] to Eqn. [4] provides the following relationship:

$$A_y/A_x = (g \cdot sin(\gamma))/(g \cdot cos(\gamma)) = tan(\gamma) \qquad [5].$$

Accordingly, the inclination or roll angle (γ) can be calculated by applying the inverse of the tangent function, i.e., the arc tan or $tan^{-1}$, to the ratio, which is to say:

$$\gamma = arc\ tan(A_y/A_x) \qquad [6].$$

Advantageously, the vertical or substantially vertical mounting and orientation of the multiple-axis accelerometer 12 ensures that by dividing $A_y$ by $A_x$, errors common to both acceleration outputs are canceled out. For example, because thermal accelerometers display predictable and repeatable variations of sensitivity resulting from temperature differentials, each acceleration output ($A_x$ and $A_y$) will exhibit the same scale change as the other. Moreover, the quotient of the ratio calculation is not affected by sensitivity changes due to temperature. In short, temperature compensation of accelerometer sensitivity is not required using the disclosed approach.

Furthermore, using the vertical reference plane 15 shown in FIG. 1 and the relationship in Eqn. [6], a positive inclination (roll) angle, e.g., acceleration into the first quadrant, will denote that the inclination (roll) is for movement attributable to a right hand or right wrist application while a negative inclination (roll) angle, e.g., acceleration into the fourth quadrant, will denote that the inclination (roll) is for movement attributable to a left hand or left wrist application. This is important because the user no longer must designate or indicate in advance that the BPM is being attached to the user's left or to the user's right wrist. Rather, the device 10 "ambidextrously" and automatically determines that the BPM associated with the device 10 is on a left wrist or a right wrist based on the polarity of the inclination (roll) angle calculation.

Multiple-Axis Accelerometer

The multiple-axis accelerometer 12, such as a MXD2020EL thermal accelerometer manufactured by MEMSIC, Inc. of Andover, Mass., can be a dual axis, linear motion sensor that is adapted to generate plural acceleration outputs ($A_x$ and $A_y$) based on the inclination of the device 10, e.g., inclination associated with a subject positioning his or her forearm, hand, and/or wrist so as to position the BPM at the elevation of the subject's myocardium.

The multiple-axis accelerometer 12 measures changes in acceleration resulting from movement of the BPM and generates therefrom acceleration data output ($A_x$ and $A_y$). The accelerometer 12 can generate analog or digital acceleration output. These data output are, in turn, transmitted to the controller unit 14 with or without conversion, e.g., analog to digital or digital to analog, or signal conditioning, e.g., filtering and the like.

Microcontroller Unit

Figure 3:
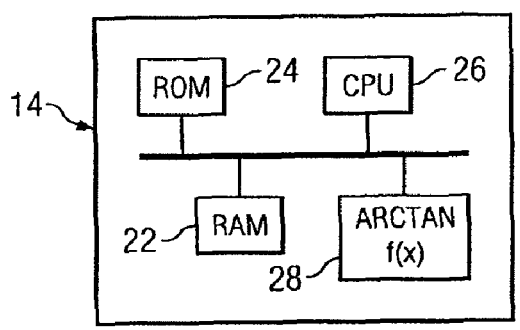
FIG. 3 shows a block diagram of a microcontroller unit in accordance with the present invention.

Referring FIG. 3, the controller 14 is adapted to convert acceleration measurement data into inclination measurement data and/or signals. To that end, the requisite controller 14 can be a microcontroller, e.g., an 8-bit or greater microcontroller, that, necessarily, includes an arc tan function, to calculate an inclination (roll) angle, e.g., using Eqn. [6], or its equivalent:

a look-up table for the arc tan function, or a mathematical approximation for the arc tan function, e.g., a Taylor series, a second or third order polynomial, and the like.

The controller 14 can include volatile memory 22 (random access memory), non-volatile memory 24 (read-only memory), and a processor or microprocessor 26 that is adapted to execute hardware- or software-based applications, driver programs, algorithms, and the like. These applications, driver programs, algorithms, which include an arc tan function 28, and the like can process and store data; calculate inclination data using acceleration output data; and determine whether the inclination denotes that the BPM is on the left or right wrist or arm, e.g., using the polarity of the inclination data.

To improve signal-to-noise ratio (SNR), the signal from the accelerometer 12 can be passed through a low-pass filter 21, to reduce noise. Alternatively, the controller unit 14 can be adapted to enhance the acceleration data. Enhancement can include, without limitation, filtering the data and compensating for any temperature variations.

Printed Circuit Board

Preferably, the multiple-axis accelerometer 12 is mounted, soldered or similarly attached to the PCB 16 so that each of the multiple-axis accelerometer's 12 sensing axes 11 and 13 lie in a common, vertical or substantially vertical plane 15. Optionally, the sensing axes 11 and 13 of the multiple-axis accelerometer 12 can be fixedly positioned to the substrate 16 to be oriented at a 45 degrees from the forward-aft axis 18 of the device 10, which axis 18 also lies in the same xy-plane 15.

Blood Pressure Measuring or Monitoring Device

Application of the inclinometer 10 and its component parts described above to a BPM will now be described. As the mammalian subject moves the device 10 that is affixed to either of his or her wrists towards the subject's myocardium, the BPM can be adapted to use acceleration data and inclination data to provide a warning signal until the BPM is properly positioned with respect to the subject's myocardium and/or to dynamically initiate operation of the cuff once the BPM is properly positioned with respect to the subject's myocardium. In contrast with prior art solutions that erroneously presume a universal relationship between the inclination (Θ) of the electronic BPM and the height differential between the elevations of the BPM and the myocardium, the use, instead, of inclination (roll) angle provides a more reliable and universal relationship for human subjects. Accordingly, the BPM of the present invention can include a pre-determined lower inclination angle (a) and a predetermined upper inclination angle (b) for the roll angle (γ).

More specifically, the BPM can be programmed so that—as with other systems known to the art—a warning signal is generated as long as the calculated or estimated inclination (roll) angle (γ) falls outside of the pre-determined lower and upper limits, i.e., γ<a or γ>b, and/or operation of the BPM is dynamically prevented until the calculated or estimated inclination (roll) angle (γ) falls between the lower and upper limits, i.e., a≦γ≦b. The intent of the former warning is to alert the mammalian subject to re-position the electronic BPM so that the roll angle falls between the pre-determined upper inclination angle (b) and pre-determined lower inclination angle (a), which limits are pre-determined to ensure that the myocardium and the BPM are more reliably at or substantially at the same elevation. The latter prevents operation of the BPM, automatically initiating the measurement or monitoring process, i.e., applying pressure to the point of fixation of the BPM, as soon as the BPM is properly aligned.

The same concept can be applied, for example, to accelerometers that use gas as a moving mass. Conventional accelerometers that measure a mechanical moving mass are biased by gravity and measurements will include error caused by the roll angle. In contrast, accelerometers using gas as the moving mass are lighter, can more easily compensate for the effects of gravity, and experience less error.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What I claim is:

1. An apparatus for measuring or monitoring blood pressure in a mammalian subject having a myocardium, the apparatus comprising:
   a sensor for detecting a pulsewave on an exterior surface of the mammalian subject and for generating data signals corresponding to the pulsewave;
   a processing unit for converting said data signals into display signals;
   an input/output interface for displaying said display signals;
   an inclination measuring device including:
   a multiple-axis accelerometer that is adapted to measure acceleration about an axis that is orthogonal or substantially orthogonal to a vertical plane in plural, orthogonal directions and to generate a first output based on an acceleration measured in a first direction ($A_x$) in the vertical plane and to generate a second output based on an acceleration measured in a second direction ($A_y$) orthogonal to the first direction in the vertical plane; and
   a controller unit that is adapted to determine a roll angle and a change in roll angle using the first and second outputs and to determine whether the device is affixed to a left wrist or to a right wrist of the mammalian subject using a polarity of the roll angle.

2. The apparatus as recited in claim 1, wherein the measured inclination is a roll angle (γ) that is given by the formula:

$$\gamma = \arctan(A_y/A_x).$$

3. The apparatus as recited in claim 1 further comprising a warning means to alert the subject when the apparatus is not properly disposed with respect to the subject's myocardium.

4. The apparatus as recited in claim 3, wherein the processing unit is further adapted to prevent the apparatus from operating until the measured roll angle is between predetermined maximum and minimum roll angles.

5. The device as recited in claim 1, wherein the multiple-axis accelerometer is a 360 degree inclinometer that is adapted to measure acceleration about the axis.

6. A method for dynamically positioning a sensor for at least one of a blood pressure measurement apparatus or a blood pressure monitoring apparatus proximate to a myocardium of a mammalian subject to provide more accurate blood pressure readings, the method comprising:
   measuring an acceleration of the blood pressure measuring or monitoring sensor in a first direction;
   measuring an acceleration of the blood pressure measuring or monitoring sensor in a second direction that is orthogonal or substantially orthogonal to the first direction;
   determining a roll angle or a change in roll angle using the first and second direction measured accelerations;

outputting a warning to alert the subject while the apparatus is not properly disposed with respect to the subject's myocardium;

preventing operation of the apparatus until the measured roll angle is between predetermined maximum and minimum roll angles; and determining whether the sensor is affixed to the left wrist or to the right wrist of the mammalian subject using a polarity of the roll angle.

7. The method as recited in claim 6, wherein the roll angle ($\gamma$) is given by the formula:

$$\gamma = \arctan(A_y/A_x)$$

in which $A_x$ corresponds to the acceleration of the blood pressure measuring or monitoring sensor in the first direction and $A_y$ corresponds to the acceleration of the blood pressure measuring or monitoring sensor in the second direction.

8. A method for dynamically determining whether a sensor for at least one of a blood pressure measurement apparatus or a blood pressure monitoring apparatus is on a left wrist or a right wrist of a mammalian subject, the method comprising:

measuring an acceleration of the blood pressure measuring or monitoring sensor in a first direction;

measuring an acceleration of the blood pressure measuring or monitoring sensor in a second direction that is orthogonal or substantially orthogonal to the first direction;

determining a roll angle or a change in roll angle using the first and second direction measured accelerations; and using polarity of the roll angle to determine whether the sensor is affixed to the left wrist or to the right wrist of the mammalian subject.

9. The method as recited in claim 8, wherein the roll angle ($\gamma$) is given by the formula:

$$\gamma = \arctan(A_y/A_x)$$

in which $A_x$ corresponds to the acceleration of the blood pressure measuring or monitoring sensor in the first direction and $A_y$ corresponds to the acceleration of the blood pressure measuring or monitoring sensor in the second direction.

* * * * *

UNITED STATES PATENT AND TRADEMARK OFFICE
CERTIFICATE OF CORRECTION

PATENT NO. : 8,211,029 B2  
APPLICATION NO. : 12/548690  
DATED : July 3, 2012  
INVENTOR(S) : Kenichi Katsumoto Page 1 of 1

It is certified that error appears in the above-identified patent and that said Letters Patent is hereby corrected as shown below:

In the Specification:

Column 4, line 14, "arc tan" should read --arctan--;

Column 4, line 17, "arc tan" should read --arctan--;

Column 4, line 66, "arc tan" should read --arctan--;

Column 5, line 1, "arc tan" should read --arctan--;

Column 5, line 2, "arc tan" should read --arctan--;

Column 5, line 9, "arc tan" should read --arctan--; and

Column 5, line 56, "$a \leqq \gamma \leqq b$" should read --$a \leq \gamma \leq b$--.

Signed and Sealed this  
Fifteenth Day of October, 2013

Teresa Stanek Rea  
*Deputy Director of the United States Patent and Trademark Office*